(12) United States Patent
Seitz

(10) Patent No.: US 6,307,097 B1
(45) Date of Patent: Oct. 23, 2001

(54) METHOD FOR PRODUCING ALUMINUM SALTS OF CYCLIC PHOSPHINIC ACIDS

(75) Inventor: Thomas Seitz, Heddesheim (DE)

(73) Assignee: Ticona GmbH (DE)

( * ) Notice: Subject to any disclaimer, the term of this patent is extended or adjusted under 35 U.S.C. 154(b) by 0 days.

(21) Appl. No.: 09/424,387

(22) PCT Filed: May 12, 1998

(86) PCT No.: PCT/EP98/02767

§ 371 Date: Mar. 6, 2000

§ 102(e) Date: Mar. 6, 2000

(87) PCT Pub. No.: WO98/52955

PCT Pub. Date: Nov. 26, 1998

(30) Foreign Application Priority Data

May 20, 1997 (DE) ............................................. 197 20 977

(51) Int. Cl.[7] .................................................. C07F 9/30
(52) U.S. Cl. ............................................. 562/19; 556/174
(58) Field of Search ............................. 562/19; 556/174; 524/116

(56) References Cited

U.S. PATENT DOCUMENTS

| | | |
|---|---|---|
| 3,594,347 | 7/1971 | Lazarus et al. . |
| 3,892,998 | 7/1975 | Tsui et al. . |
| 3,900,444 | 8/1975 | Racky et al. . |
| 3,953,539 | 4/1976 | Kawase et al. . |
| 4,036,811 | 7/1977 | Noetzel et al. . |
| 4,049,612 | 9/1977 | Sandler . |
| 4,078,016 | 3/1978 | Kramer . |
| 4,180,495 | 12/1979 | Sandler . |
| 4,208,321 | 6/1980 | Sandler . |
| 4,208,322 | 6/1980 | Sandler . |
| 5,780,534 | 7/1998 | Kleiner et al. . |
| 6,087,423 * | 7/2000 | Kleiner et al. ........................ 524/116 |

FOREIGN PATENT DOCUMENTS

| | | |
|---|---|---|
| 700 042 | 7/1967 | (BE) . |
| 2 102 841 | 8/1971 | (DE) . |
| 2 252 256 | 5/1974 | (DE) . |
| 2 252 258 | 5/1974 | (DE) . |
| 2 447 727 | 4/1976 | (DE) . |
| 2 915 116 | 10/1979 | (DE) . |
| 006 568 | 1/1980 | (EP) . |
| 2 827 867 | 1/1980 | (DE) . |
| 452 755 | 10/1991 | (EP) . |
| 458 067 | 11/1991 | (EP) . |
| 699 708 | 3/1996 | (EP) . |
| 794 191 | 9/1997 | (EP) . |
| 0794191 * | 9/1997 | (EP) . |
| 2 204 659 | 10/1972 | (FR) . |
| 2 422 698 | 4/1978 | (FR) . |

OTHER PUBLICATIONS

Derwent English Abstract (1971–52012S) for DE 2 102 841 (Aug. 5, 1971).
Derwent English Abstract (1974–C6071V) for DE 2 252 256 (May 9, 1974).
Derwent English Abstract (1974–34563V) for DE 2 252 258 (May 9, 1974).
Derwent English Abstract (1976–28565X) for DE 2 447 727 (Apr. 8, 1976).
Derwent English Abstract (1979–59863B) for DE 2 915 116 (Oct. 25, 1979).
Derwent English Abstract (1980–02156C) for DE 2 827 867 (Jan. 17, 1980).
Derwent English Abstract (1980–02156C) for EP 006 568 (Jan. 9, 1980).
Derwent English Abstract (1991–312047) for EP 452 755 (Oct. 23, 1991).
Derwent English Abstract (1991–347511) for EP 458 067 (Nov. 27, 1991).
Derwent English Abstract (1996–130732) for EP 699 708 (Mar. 6, 1996).
Derwent English Abstract (1997–437433) for EP 794 191 (Sep. 10, 1997).
Derwent English Abstract (1974–34563V) for FR 2 204 659 (Oct. 25, 1972).
Derwent English Abstract (1979–59863B) for FR 2 422 698 (Apr. 13, 1978).
Derwent English Abstract (1976–42858X) for JP 51 047035 and JP 82 059262 (Apr. 22, 1976).

* cited by examiner

*Primary Examiner*—Jean F. Vollano
(74) *Attorney, Agent, or Firm*—Connolly Bove Lodge & Hutz LLP

(57) ABSTRACT

A process for the preparation of aluminum salts of cyclic phosphinic acids is described, which comprises reacting cyclic phosphinic acids, such as 1-hydroxydihydrophosphole oxides or 1-hydroxyphospholane oxides, with aluminum hydroxide in the presence of water and in the absence of polar solvents at elevated temperature for a reaction time of from 1 to 20 hours.

18 Claims, No Drawings

METHOD FOR PRODUCING ALUMINUM SALTS OF CYCLIC PHOSPHINIC ACIDS

This application is a 371 of PCT/EP98/02767, filed May 12, 1998, now WO98/52955.

BACKGROUND OF THE INVENTION

1. Field of the Invention

The invention relates to a process for the preparation of aluminum salts of cyclic saturated or unsaturated phosphinic acids, in particular aluminum salts of 1-hydroxydihydrophosphole oxides and 1-hydroxyphospholane oxides.

2. Description of the Prior Art

Salts of phosphinic acids have already been known per se for some time and are recommended in particular as flame-inhibiting additives for thermoplastics such as polyesters or polyamides. Thus, DE-A1-2252258 describes alkali metal salts of phosphinic acids. They must, however, be added in relatively large amounts and some have an unfavorable corrosion-promoting influence on the processing machinery.

EP-A3-0699708 discloses polyester molding compositions which contain calcium salts or aluminum salts of phosphinic acids of the following formulae:

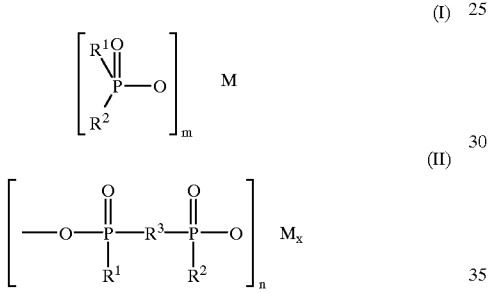

wherein $R^1$ and $R^2$ are $C_1$–$C_6$-alkyl, linear or branched; phenyl;

$R^3$ is $C_1$–$C_{10}$-alkylene, linear or branched; arylene; alkylarylene; or arylalkylene;

M is a calcium ion or aluminum ion;

m is 2 or 3;

n is 1 or 3; and x is 1or 2.

The preparation of the aluminum salts, described in this European patent application, of the phosphinic acids mentioned therein requires a relatively long reaction time, namely 24, or even 65, hours.

Although a large number of phosphinic acid compounds and preparation processes for these compounds are already known, there is still a need for improved processes for the preparation of suitable phosphinic acid salts which may be used as agents for improving the flame resistance of plastics.

The object of the invention is thus to provide a process in which it is possible to prepare desirable phosphinic acid salts which may be used as flameproofing agents; the object of the invention is also to provide a process which is economical and which leads to high yields in short reaction times. The object of the invention is also to provide a process which is environmentally friendly and which produces no or only small amounts of substances which must be removed during isolation of the final product and be disposed of.

SUMMARY OF THE INVENTION

This object is achieved by a process for the preparation of aluminum salts of cyclic phosphinic acids, which comprises reacting cyclic phosphinic acids with aluminum hydroxide in the presence of water and in the absence of polar solvents at elevated temperature for a reaction time of from 1 to 20 hours. The reaction is preferably carried out for a period of from 1 to 10, in particular from 3 to 7, hours. Particularly advantageous reaction temperatures are from 50 to 200° C., in particular from 80 to 100° C. It is advantageous to react 1 mole of acid with ⅓ of a mole of aluminum hydroxide in the presence of from 0.5 to 3 ml of water, calculated per gram of acid; from 1 to 2 ml of water are preferably used per gram of acid.

DESCRIPTION OF THE PREFERRED EMBODIMENTS

The cyclic phosphinic acids used to react with aluminum hydroxide are preferably 1-hydroxydihydrophosphole oxides of the formula Ia or Ib and 1-hydroxyphospholane oxides of the formula Ic or mixtures thereof,

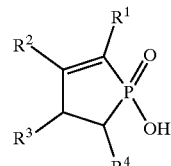

(Ia)

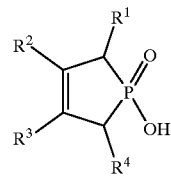

(Ib)

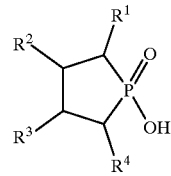

(Ic)

in which $R^1$, $R^2$, $R^3$, $R^4$ are hydrogen or alkyl, preferably $C_1$–$C_{12}$-alkyl, in particular $C_1$–$C_4$-alkyl, preferably methyl or ethyl.

The reaction may be carried out under pressure, and is preferably carried out in an autoclave under autogenous pressure.

The cyclic phosphinic acids used according to the invention can be obtained by hydrolysis of the corresponding cyclic chlorine compounds. Thus, the preparation of 1-chlorodihydrophosphole oxide and hydrolysis of this compound to 1-hydroxydihydrophosphole oxide is described by Kurt Moedritzer in SYN. REACT. INORG. METAL-ORG. CHEM., 5(1), 45–58 (1975). Another synthesis for preparing such chlorine compounds can be found in EP-A1-0452755. The saturated cyclic phosphinic acids can be obtained by hydrogenating the corresponding unsaturated cyclic phosphinic acids.

To prepare the corresponding aluminum salts, the phosphinic acids are dissolved in water and reacted with aluminum hydroxide. If it is not absolutely necessary to carry out the reaction in exactly stoichiometric proportions, it is advantageous to use ⅓ of a mole of aluminum hydroxide per mole of acid. The amount of water used in the reaction can also vary within wide limits. It is, however, advantageous to use from about 1 to 2 ml of water per gram of acid used.

The reaction is carried out at elevated temperature, the reaction mixture advantageously being stirred during the reaction. It is advantageous to maintain a temperature of at least 50° C. and a very suitable temperature range is from 80 to 100° C.

The reaction can also be carried out very successfully under pressure, pressures of from 2 to 10 bar being particularly advantageous.

The reaction can also be carried out at temperatures above 100° C., temperatures of up to 200° C. being particularly advantageous.

Cyclic phosphinic acids which are suitable for the novel process and have proven successful include the following compounds:

1-Hydroxy-3-methyl-2,5-dihydro-1H-phosphole 1-oxide, 1-hydroxy-3-methyl-1H-phospholane 1-oxide, 1-hydroxy-2,3-dihydro-1H-phosphole 1-oxide, 1-hydroxy-2,5-dihydro-1H-phosphole 1-oxide and 1-hydroxy-1H-phospholane 1-oxide.

The times for the reaction of the invention are generally at most 20 hours, but are in most cases considerably less than this; it is advantageous to carry out the reaction within a period of from 1 to 10 hours, in particular from 3 to 7 hours. It is also very advantageous to carry out the reaction in an autoclave under autogenous pressure, i.e. the reaction components cyclic phosphinic acid, aluminum hydroxide and water are introduced into an autoclave where they are reacted under autogenous pressure, i.e. the reaction mixture is heated in the autoclave in a closed system so that the reaction is carried out under the pressure which arises during heating.

The reaction is carried out without the addition of polar solvents such as acetic acid, propionic acid, methanol, ethanol, propanol, butanol, acetone, methyl ethyl ketone, tetrahydrofuran, dioxane, acetonitrile and the like.

It was particularly surprising that it is possible, using the novel process, to prepare the desirable aluminum salts of cyclic saturated and unsaturated phosphinic acids within short reaction times. In contrast to the long reaction times of 24 or 65 hours, as required for the preparation of aluminum salts of noncyclic salts of phosphinic acids, the reaction times of the invention are significantly shorter. In most cases, a reaction time of at most 7 hours is sufficient to obtain very high yields.

The process gives very desirable aluminum salts of cyclic phosphinic acids, which can be used in particular as flame retardants for plastics such as polyamides, in particular polyesters.

Since the reaction requires just 3 components, namely the phosphinic acid, aluminum hydroxide and water, the process is also very environmentally friendly; removal and disposal of byproducts or undesired substances, such as organic solvents, is not necessary.

The invention is illustrated in more detail by the following examples:

EXAMPLE 1

Aluminum Salt of the Isomeric Mixture of 1-hydroxy-2,5-dihydro-1H-phosphole 1-oxide and 1-hydroxy-2,3-dihydro-1H-phosphole 1-oxide (4:1)

10.0 g (84.7 mMol) of a mixture of 1-hydroxy-2,5-dihydro-1H-phosphole 1-oxide and 1-hydroxy-2,3-dihydro-1H-phosphole 1-oxide (in the ratio 4:1) are dissolved in 16 ml of water. At 80° C., 2.2 g (27.8 mMol) of aluminum hydroxide are added and the suspension is stirred at from 85 to 90° C. for the stated reaction times. The precipitate is then filtered off with suction at about 60° C. and dried at 140–150° C. in a vacuum drying cabinet. The reaction product is obtained as a pale yellow powder having an m.p. of >380° C.

| No. 1 | Reaction time [h] | Yield [g] | Yield [% of theory] |
|---|---|---|---|
| a | 1 | 9.0 | 84 |
| b | 3 | 10.7 | 100 |
| c | 5 | 10.7 | 100 |
| d | 7 | 10.7 | 100 |

EXAMPLE 2

Aluminum Salt of 1-hydroxy-1H-phospholane 1-oxide 10.0 g (83.3 mMol) of 1-hydroxy-1H-phospholane 1-oxide are dissolved in 16 ml of water. At 80° C., 2.2 g (27.8 mMol) of aluminum hydroxide are added and the suspension is stirred at from 85 to 90° C. for the stated reaction times. The precipitate is then filtered off with suction at about 60° C. and dried at 140–150° C. in a vacuum drying cabinet. The reaction product is obtained as a colorless powder having an m.p. of >380° C.

| No. 2 | Reaction time [h] | Yield [g] | Yield [% of theory] |
|---|---|---|---|
| a | 1 | 6.4 | 60 |
| b | 2 | 8.5 | 80 |
| c | 3 | 9.7 | 91 |
| d | 5 | 9.8 | 92 |
| e | 7 | 9.8 | 92 |

EXAMPLE 3

Aluminum Salt of 1-hydroxy-3-methyl-1H-phospholane 1-oxide 10.0 g (75.7 mMol) of 1-hydroxy-3-methyl-1H-phospholane 1-oxide are dissolved in 16 ml of water. At 80° C., 2.0 g (25.2 mMol) of aluminum hydroxide are added and the suspension is stirred at from 85 to 90° C. for the stated reaction times. The precipitate is then filtered off with suction at about 60° C. and dried at 140–150° C. in a vacuum drying cabinet. The reaction product is obtained as a colorless powder having an m.p. of >380° C.

| No. 3 | Reaction time [h] | Yield [g] | Yield [% of theory] |
|---|---|---|---|
| a | 1 | 9.8 | 92 |
| b | 2 | 9.8 | 92 |
| c | 3 | 9.9 | 93 |
| d | 5 | 10.0 | 94 |
| e | 7 | 10.2 | 96 |

COMPARATIVE EXAMPLE 1 (No. 4)

Aluminum Salt of Ethylmethylphosphinic Acid (Comparative Example)

10.0 g (92.5 mMol) of ethylmethylphosphinic acid are dissolved in 16 ml of water. At 80° C., 2.4 g (30.8 mMol) of aluminum hydroxide are added and the suspension is stirred at from 85 to 90° C. for the stated reaction times. The precipitate is then filtered off with suction at about 60° C. and dried at 140–150° C. in a vacuum drying cabinet. The reaction product is obtained as a colorless powder having an m.p. of >380° C.

| No. 4 | Reaction time [h] | Yield [g] | Yield [% of theory] |
|---|---|---|---|
| a | 3 | 9.8 | 66 |
| b | 5 | 9.8 | 70 |
| c | 7 | 9.9 | 80 |
| d | 15 | 10.0 | 86 |
| e | 20 | 10.2 | 94 |
| f | 50 | 10.2 | 94 |

COMPARATIVE EXAMPLE 2 (No. 5)

Aluminum Salt of N-butylmethylphosphinic Acid (Comparative Example)

10.0 g (73.5 mMol) of n-butylmethylphosphinic acid are dissolved in 16 ml of water. At 80° C., 1.9 g (24.5 mMol) of aluminum hydroxide are added and the suspension is stirred at from 85 to 90° C. for the stated reaction times. The precipitate is then filtered off with suction at about 60° C. and dried at 140–150° C. in a vacuum drying cabinet. The reaction product is obtained as a colorless powder having an m.p. of >380° C.

| No. 5 | Reaction time [h] | Yield [g] | Yield [% of theory] |
|---|---|---|---|
| a | 3 | 7.9 | 75 |
| b | 5 | 8.0 | 76 |
| c | 7 | 8.5 | 80 |
| d | 15 | 9.6 | 91 |
| e | 20 | 9.6 | 91 |
| f | 50 | 9.7 | 92 |

What is claimed is:

1. A process for preparing an aluminum salt of a cyclic phosphinic acid which comprises reacting the cyclic phosphinic acid with aluminum hydroxide in the presence of water and in the absence of a polar solvent selected from the group consisting of acetic acid, propionic acid, methanol, ethanol, propanol, butanol, acetone, methyl ethyl ketone, tetrahydrofuran, dioxane and acetonitrile at an elevated temperature for a reaction time of from 1to 7 hours.

2. A process for preparing an aluminum salt of a cyclic phosphinic acid, which comprises reacting the cyclic phosphinic acid with aluminum hydroxide in the presence of water and in the absence of a polar solvent selected from the group consisting of acetic acid, propionic acid, methanol, ethanol, propanol, butanol, acetone, methyl ethyl ketone, tetrahydrofuran, dioxane and acetonitrile at an elevated temperature for a reaction time of from 1 to 20 hours and wherein the process is carried out in an autoclave.

3. The process as claimed in claim 2, wherein the reaction time is from 3 to 7 hours.

4. The process as claimed in claim 2, wherein the elevated temperature is from 80 to 100° C.

5. The process as claimed in clam 2, wherein one mole of the cyclic phosphinic acid is reacted with ⅓ of the mole of the aluminum hydroxide in the presence of from 0.5 to 3 ml of the water, calculated per gram of acid.

6. The process as claimed in claim 5, wherein from about 1 to 2 ml of the water are used per gram of acid.

7. The process as claimed in claim 2, wherein the cyclic phosphinic acid is a 1-hydroxydihydrophosphole oxide of the formula (Ia), a 1-hydroxydihydrophosphole oxide of the formula (Ib), a 1-hydroxyphospholane oxide of the formula Ic), or a mixture thereof,

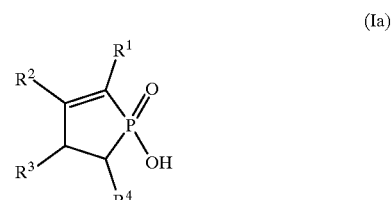

(Ia)

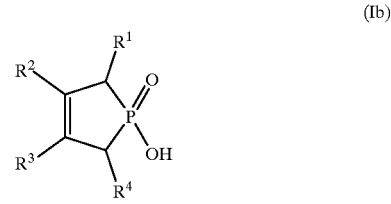

(Ib)

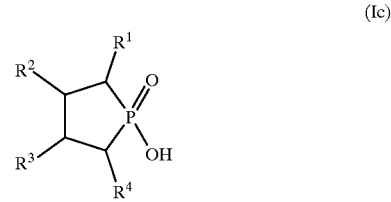

(Ic)

in which
$R^1$, $R^2$, $R^3$ and $R^4$, independently of one another, are hydrogen or an alkyl group.

8. The process as claimed in claim 1, wherein the reaction is pressurized.

9. A process for preparing an aluminum salt of a cyclic phosphinic acid, which comprises reacting the cyclic phosphinic acid with aluminum hydroxide in the presence of water and in the absence of a polar solvent selected from the group consisting of acetic acid, propionic acid, methanol, ethanol, propanol, butanol, acetone, methyl ethyl ketone, tetrahydrofuran, dioxane and acetonitrile at an elevated temperature for a reaction time of from 1 to 10 hours and wherein the reaction is carried out in an autoclave under an autogenous pressure.

10. The process as claimed in claim 7, wherein the alkyl group is a $C_1$–$C_{12}$-alkyl group.

11. The process as claimed in claim 10, wherein the alkyl group is a $C_1$–$C_4$-alkyl group.

12. The process as claimed in claim 11, wherein the alkyl group is a methyl group or an ethyl group.

13. The process as claimed in claim 2, wherein the elevated temperature is from 50 to 200° C.

14. The process as claimed in claim 2, wherein the pressure is from 1 to 5 bar.

15. A process for preparing an aluminum salt of a cyclic phosphinic acid, which comprises reacting the cyclic phosphinic acid with aluminum hydroxide in the presence of water and in the absence of a polar solvent selected from the group consisting of acetic acid, propionic acid, methanol, ethanol, propanol, butanol, acetone methyl ethyl ketone, tetrahydrofuran, dioxane and acetonitrile at an elevated temperature for a reaction time of from 1 to 10 hours and at a pressure from 2 to 10 bar.

16. The process as claimed in claim 7, wherein the cyclic phosphinic acid is at least one of the following compounds:

1-hydroxy-3-methyl-2,5-dihydro-1H-phosphole 1-oxide,
1-hydroxy-3-methyl-1H-phospholane 1-oxide,
1-hydroxy-2,3-dihydro-1H-phosphole 1-oxide,
1-hydroxy-2,5-dihydro-1H-phosphole 1-oxide and
1-hydroxy-1H-phospholane 1-oxide.

17. The process as claimed in claim 2, wherein the elevated temperature is above 100° C. to 200° C.

18. The process as claimed in claim 2, wherein the pressure is from 2 to 10 bar.

* * * * *